(12) United States Patent
Amzallag et al.

(10) Patent No.: US 12,232,927 B2
(45) Date of Patent: Feb. 25, 2025

(54) INTERACTIVE DENTAL TREATMENT PLANNING

(71) Applicant: Clevaligner Ltd, Jerusalem (IL)

(72) Inventors: Yehiel Amzallag, Netanya (IL);
Jonathan Tabet, Jerusalem (IL)

(73) Assignee: CLEVALIGNER LTD, Jerusalem (IL)

( * ) Notice: Subject to any disclaimer, the term of this patent is extended or adjusted under 35 U.S.C. 154(b) by 0 days.

(21) Appl. No.: 18/630,529

(22) Filed: Apr. 9, 2024

(65) Prior Publication Data
US 2025/0025264 A1    Jan. 23, 2025

Related U.S. Application Data

(60) Provisional application No. 63/527,761, filed on Jul. 19, 2023.

(51) Int. Cl.
*A61C 7/00* (2006.01)
*A61C 13/34* (2006.01)

(52) U.S. Cl.
CPC .............. *A61C 7/002* (2013.01); *A61C 13/34* (2013.01)

(58) Field of Classification Search
CPC .................................. A61C 7/002; A61C 13/34
See application file for complete search history.

(56) References Cited

U.S. PATENT DOCUMENTS

| | | | |
|---|---|---|---|
| 9,390,063 B2 | 7/2016 | Hultgren | |
| 10,896,761 B2 | 1/2021 | Stone-Collonge | |
| 10,898,299 B2 | 1/2021 | Boltunov | |
| 2007/0099147 A1* | 5/2007 | Sachdeva | A61C 9/0046 433/24 |
| 2022/0338966 A1* | 10/2022 | Lancelle | A61B 90/36 |
| 2022/0378549 A1 | 12/2022 | Blanco | |

\* cited by examiner

*Primary Examiner* — Bobbak Safaipour
(74) *Attorney, Agent, or Firm* — Marc Van Dyke; Momentum IP

(57) ABSTRACT

Orthodontic and/or dental treatment planning methods and systems are presented. The methods and systems are configured to receive an initial patient dentition and generate a proposed-state dentition model. The processor is further configured to display, in two dimensions, the proposed-state dentition model superimposed on the initial patient dentition model. A user-interface enables a user to modify or repeatedly modify the one or more of an arch form, anteroposterior correction, overjet correction, transverse dimension, midline, or interproximal reduction information while a display enables presenting the result in real-time. Specifically disclosed is a method enabling a user to modify or repeatedly modify an arch form, wherein feedback on interproximal reduction is provided in real time. A user-interface is further configured to enable selection by the user of a modified treatment plan.

20 Claims, 4 Drawing Sheets

INTERACTIVE DENTAL TREATMENT PLANNING

CROSS-REFERENCE TO RELATED APPLICATIONS

This patent application claims priority to U.S. Provisional Patent Application No. 63/527,761, titled "INTERACTIVE DENTAL TREATMENT PLANNING," filed on Jul. 19, 2023, and herein incorporated by reference in its entirety.

FIELD OF THE INVENTION

The present invention is related to the field of orthodontics, and more particularly to a computer-implemented method and system for interactive digital orthodontic treatment planning.

BACKGROUND OF THE INVENTION

Patient-removable appliances, such as aligners, have become an important tool for treating malocclusions and other dental problems in orthodontics and dentistry. Treatment planning typically involves inputting initial patient dentition information, creating a model of a target state configuration of the patient's teeth, and planning the transition from an initial state to target state dentition with a series of successive stages. Each stage would correspond to an individual patient-removable appliance, such as an aligner, which is worn sequentially. Each appliance is designed to gradually direct teeth such that they are moved relative to the prior stage until the teeth are in the target configuration. The plan would also include some indication of the duration of time each appliance is to be worn. Once in the target configuration, the final stage may involve a retainer to maintain the target configuration for some retaining duration.

In the past, orthodontic treatment plans were automatically generated and typically provided as a single, fixed plan for modifying a patient's dentition from an initial position to a final position. Recent advances have introduced the possibility of inputting information based on the preferences of the dental professional or patient prior to the automatic generation of the treatment plan. Typically, the nature of the input is a binary Boolean input (e.g., yes/no). This process involves using a multi-objective optimization model that considers medical parameters such as teeth movement restrictions, antero-posterior correction, horizontal overjet, deep bite, midline correction (i.e., right/left) and stripping interocclusal record plate (i.e., posterior/anterior).

Despite advancements in multi-objective optimization, current approaches rely heavily on automated algorithm specifications provided by a processor and do not fully consider dental practitioner or patient needs in the process of automated orthodontic treatment planning. More recently, it has become possible to have a dental professional modify the plan and send it back for additional processing and update of the treatment plan, iterating this process until a final treatment plan is completed and then provided to the patient. This modification process typically requires, at minimum, a couple of days, which adds delay to the overall workflow and requires repeated coordination and visits by the patient. Because multiple parties are involved, the overall process is inefficient and is far from a chairside application.

Real-time appliance design, enabling the medical practitioner to make interactive numeric adjustments during the processing stage, is lacking. In addition, selection of an optimal shape of an arch form, which balances risk with personal preference of a patient has not been addressed. The technical means to effectively assist the dental practitioner in providing the most appropriate plan, that is, one that achieves a personalized, patient-centered, risk-benefit balance, is currently lacking in the field. In order to achieve this balance, a more versatile approach that goes beyond inputting parameters in an algorithm at the start of treatment is needed.

Thus, there is a need in the art for a system and method of preparing a dental treatment plan which maintains efficiency by employing processor capabilities such as computational speed and exhaustive and accurate processing while also integrating control and selection by an experienced practitioner with a patient, skills, experience, flexibility, and judgment of an experienced practitioner. This would allow for more accurate feedback on a practitioner as well as a synergistic selection of the most appropriate treatment and accurate processing, for a synergistic selection of the most appropriate treatment.

SUMMARY OF THE INVENTION

Described herein are systems and methods for integrating control and selection by the experienced practitioner of a dental treatment plan for a given patient. In one aspect, there is provided a computer-implemented method for interactive digital orthodontic treatment planning, executed by a processor; said method involving receiving in a processor a digital representation of an initial patient dentition (i.e., model). The method may further involve generating a proposed-state dentition mode, proposed interproximal reduction information, and proposed related information. The method may further include displaying the proposed-state dentition model in a two-dimensional digital representation superimposed on the initial patient dentition model, proposed interproximal reduction information as well as other proposed related information (e.g. arch form). In some embodiments, related information may include any one or more of a proposed: arch form, interproximal reduction information, anteroposterior correction, overjet correction, transverse dimension, and midline. In some embodiments, the related information may be selectively displayed. In some embodiments, related information includes all of the following: a proposed arch form, interproximal reduction information, anteroposterior correction, overjet correction, transverse dimension, and midline. The method may further include a step (i.e., step iv.) of receiving, via a user-interface, one or more user-directed modifications to the proposed arch form, anteroposterior correction, overjet correction, transverse receiving, via a user-interface, one or more user-directed modifications dimension, midline, or interproximal reduction information and, in real time, displaying a resulting two-dimensional user-modified dentition model superimposed on the initial patient dentition model. In other embodiments, receiving, via a user-interface, one or more user-directed modifications to the proposed arch form, anteroposterior correction, overjet correction, transverse dimension, midline, and, in real time, displaying a resulting two-dimensional user-modified dentition model superimposed on the initial patient dentition model and with associated interproximal reduction information. In other embodiments, displaying may include displayed a resulting two-dimensional user-modified dentition model superimposed on another user-modified dentition model resulting from alternation in any one of the proposed arch form, interproximal reduction information, anteroposterior correction, overjet correction, transverse dimension, and midline. The method may further include optionally, repeating the previous step iv one or more times. The method may further include receiving, via the user-interface, a user selection of a user-modified dentition model. The method may further include generating a digital orthodontic treatment plan based on a user-selected dentition model. A digital orthodontic treatment plan may include providing output, including digital parameters, to construct a sequence of aligners to be worn in successive stages. In this case, each aligner is configured to direct a movement of a patient dentition to successive stages from the initial patient dentition model to a user-selected dentition model.

In another aspect, there is provided a system for interactive digital orthodontic treatment planning including a processor, a user-interface, a memory coupled to the processor, wherein the memory is configured to direct the processor. In some embodiments, the user-interface is configured for user-directed modification of one or more of the proposed arch forms, anteroposterior, overjet, transverse dimension, midline or interproximal reduction information and selection of a user-modified dentition model resulting from modifications as well as user-selection of a user-modified dentition model.

In another aspect, there is provided, computer-implemented method for interactive digital orthodontic treatment planning executed by a processor, said method comprising: receiving in a processor, a digital representation of an initial patient dentition model; generating a proposed perturbed-state dentition model; displaying proposed interproximal reduction information and, further displaying a two dimensional proposed perturbed-state dentition model having a proposed arch form, wherein the proposed perturbed-state dentition model is superimposed on the initial patient dentition model; receiving, via a user-interface, one or more user-directed modifications to the proposed arch form or the proposed interproximal reduction information and, in real time, displaying a resulting user-modified perturbed-state dentition model superimposed on the initial patient dentition model; optionally, repeating step iv one or more times; receiving, via the user-interface, a user selection of a user-modified perturbed-state dentition model; and generating a digital orthodontic treatment plan based on a user-selected user-modified perturbed-state dentition model. In some embodiments, the memory is configured to direct the processor to: receive in a processor, a digital representation of an initial patient dentition; generate a proposed dentition model; display a proposed interproximal reduction information and, in two dimensions, the proposed dentition model having a proposed arch form, and being superimposed on an initial patient dentition model; optionally, further displaying any one or more of a proposed anteroposterior correction, overjet correction, transverse dimension, and midline; receive, via a user-interface, user-selected modifications of proposed one or more of an arch form, anteroposterior, overjet, transverse dimension, midline or interproximal reduction information and selection of a user-modified dentition model resulting from modifications; and, in real time, displaying a resulting user-modified dentition model superimposed on the initial patient dentition model; optionally, repeating step iv one or more times; receive, via the user-interface, a user selection of a user-modified dentition model; and generate a digital orthodontic treatment plan based on a user-selected dentition.

In various embodiments of the methods or systems described herein, receiving the digital representation of the initial patient dentition involves receiving a three-dimensional digital representation. In various embodiments of the methods or systems described herein, in addition to displaying the proposed dentition model in a two-dimensional digital representation, the method further provides displaying any one or more, two or more or three or more of the following: anteroposterior correction, overjet correction, transverse dimension, and midline.

In various embodiments of the methods or systems described herein, displaying may be on a screen, also known as a monitor.

In various embodiments of the methods or systems described herein, displaying further includes an arch form for the initial patient dentition.

In various embodiments of the methods or systems described herein, displaying the proposed interproximal reduction information, includes displaying a total sum of the interproximal reduction information of an upper or lower dentition.

In various embodiments of the methods or systems described herein, displaying the proposed interproximal reduction information, includes displaying a sum of the interproximal reduction information on a per tooth basis. In various embodiments of the methods or systems described herein, displaying the proposed interproximal reduction information, includes displaying the sum of the interproximal reduction information on a per tooth basis, broken down into mesial and distal tooth surface.

In various embodiments of the methods or systems described herein, displaying the proposed interproximal reduction information, includes displaying a sum of reduction on a half arch basis.

In various embodiments of the methods or systems described herein, displaying further includes displaying, in a second region, the digital representation of the proposed or user-modified dentition model arch form and opposing dentition model arch form. Opposing, in this context, refers to the upper dentition when the lower dentition is the focus of the digital representation of the user-modified dentition.

In various embodiments of the methods or systems described herein, displaying further comprises displaying in a second region, the digital representation of the proposed or user-modified dentition model arch form and opposing dentition arch form.

In various embodiments of the methods or systems described herein, receiving, via user-interface, one or more user-directed modifications. The user-directed modifications may be one or more of the following: expansion or contraction of the arch form, shifting a center of an arch form, interproximal reduction on a dentition, interproximal reduction on a per tooth basis, or interproximal reduction per mesial or distal surfaces of the tooth. For example, a user-directed modification may be an expansion or contraction of an arch form at one or more locations or shifting a center of an arch form and applying expansion or contraction. In another example, a user-directed modification in the interproximal reduction information may be, on a per tooth basis, per mesial surface of an individual tooth, or per distal surface of an individual tooth.

In various embodiments of the methods or systems described herein, receiving, via the user-interface, one or more user-directed modifications to the interproximal reduction may be information such as adding or subtracting an amount from the interproximal reduction on a per tooth basis, per mesial surface of an individual tooth, or per distal surface of an individual tooth.

In various embodiments of the methods or systems described herein, a user-directed modification includes expansion or contraction of an arch form at one or more locations or shifting a center of the arch form and applying expansion or contraction.

In various embodiments of the methods or systems described herein, the system or method may include displaying in an additional region, a two-dimensional digital representation of the proposed-state dentition which may include the proposed arch form and proposed interproximal reduction information, wherein the interproximal reduction information is a sum of reduction on a total dentition.

In various embodiments of the methods or systems described herein, the system or method may include displaying, in an additional region, a two or three-dimensional view of initial, proposed or user-modified state of an upper and lower side view of a patient dentition, upper and lower side view of a face, or upper and lower jaw radiographic view.

In various embodiments of the methods or systems described herein, the system or method may include, receiving, via the user-interface, one or more user-directed modifications to the anteroposterior correction being modified with numerical values for factor teeth relationships. This includes, not only indicating the desired class (e.g., Class I, Class II), but also allowing precise adjustment with numerical values for factors such as teeth relationship, including canine and molar relationships. Class, in this context, refers to the classification given to a given malocclusion based on Edward Angle's classification system. This feature is particularly beneficial for complex cases, including asymmetrical cases, where precise correction is essential.

In various embodiments of the methods or systems described herein, the system or method may include, receiving, via the user-interface, one or more user-directed modifications to the transverse dimension by specifying the desired range of expansion, or providing control over the width of the dental arch to achieve optimal alignment and occlusion.

In various embodiments of the methods or systems described herein, the system or method may include, receiving, via the user-interface, one or more user-directed modifications to the overjet correction by modifying the horizontal overlap between the upper and lower teeth. The user-interface may allow users to specify precise targets for correcting the horizontal overlap between the upper and lower teeth. This adjustment can be implemented for both the upper and lower jaws, for optimal dental alignment and bite.

In various embodiments of the methods or systems described herein, the system or method may include, receiving, via the user-interface, one or more user-directed modifications to the proposed midline by modifying the horizontal overlap between the upper and lower dentition. The user-interface allows users to specify the alignment of the incisor midline between the upper and lower dentition. This ensures symmetry and proper alignment of the dental arches, enhancing overall aesthetics and functionality.

In various embodiments of the methods or systems described herein, the system or method may include displaying, in an additional region, a two or three-dimensional view of the initial, proposed or user-modified state of an upper and lower side view of a dentition, upper and lower side view of a face, or upper and lower jaw radiographic view.

In various embodiments of the methods or systems described herein, the system or method may include toggling by the user-interface, between each user-modified dentition model, which enables the user to view multiple user-modified dentition models during the process of selection. In some embodiments, the user-modified dentition model may be superimposed on the initial patient dentition model or alternative user-modified dentition model.

In various embodiments of the methods or systems described herein, the system of the method may include displaying, in an additional region, an initial occlusion relationship having a two-dimensional initial and proposed-state dentition and a user-modified occlusion relationship having a two-dimensional initial and user-modified dentition model.

In various embodiments of the methods or systems described herein, the system or method may include providing an output for a digital orthodontic treatment plan. For example, the system or method may include generating the digital orthodontic treatment plan based on a user-selected dentition model wherein it includes providing digital parameters to construct a sequence of aligners to be worn in successive stages, each aligner directing a movement of a patient dentition to a successive stage from the initial patient dentition to the user-selected dentition model. In various embodiments, the method further includes transmitting to a remote site for generating of an array of aligners.

DETAILED DESCRIPTION

Figure 1:
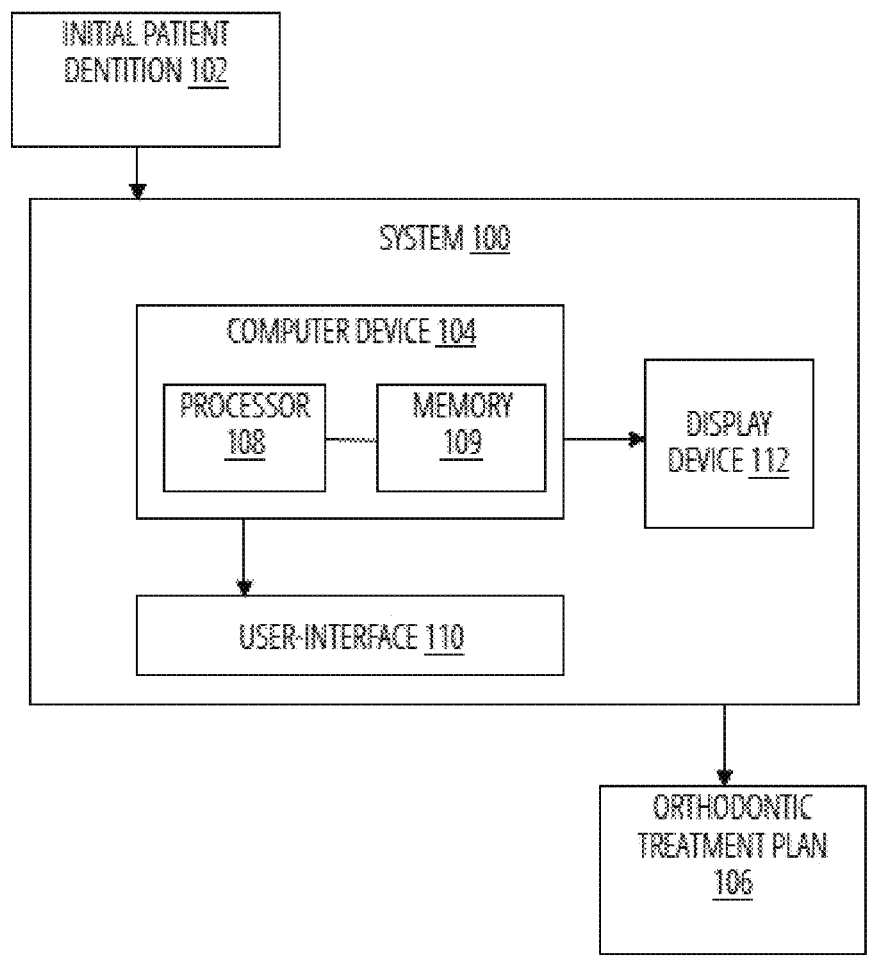
FIG. 1 shows one exemplary representation, by way of a block diagram, of an overall system for interactive digital orthodontic treatment planning for implementing various embodiments of the methods of the present invention.

The present invention relates to a method and system for interactive digital orthodontic treatment planning. The described method and system enable user-directed modifications of specific parameters of an automatically generated proposed dentition model as well as facilitate the selection of digital treatment planning based on real-time adjustment between the different user-modified dentition models. In this way, a dental practitioner can modify multiple parameters which may be personalized for a patient while also optimizing a risk-benefit ratio using the ability to view the user-modified models in a way that credibly assists in selecting an optimal personalized dentition treatment.

Embodiments of the present disclosure, in a synergistic manner, integrate skills of a human operator with computer capabilities. This incorporates the advantage of human skills of creativity, use of heuristics, flexibility, and judgment, and combines these with computer-based advantages, such as speed of computation, capability for exhaustive and accurate processing, and reporting and data access capabilities.

An additional advantage may be to improve the interaction between the dental practitioner or patient during the course of planning by providing user-directed modification of specific parameters and tools for visual assessment of a specific change, especially relating to arch form and interproximal reduction information. This approach allows for more personalized and effective risk-benefit analysis, leading to a better selection of the most appropriate dental treatment plan.

The following detailed description should be read in conjunction with the drawings, where identical reference numbers are employed to identify elements across various figures. The drawings, which may not be to scale, as well as thorough explanations show a few examples of the invention and are not meant to be taken as limiting its use. Explanations of the invention's various embodiments, adaptations, variants, alternatives, and uses-including what is currently thought to be the best way to implement it-will make it evident to one of ordinary skill in the art how to produce and utilize it.

It should be noted that, unless the context clearly indicates otherwise, the singular forms "a," "one," "an," and "the" are often used for simplicity; singular forms include the plural unless the singular alone is explicitly stated or clear from the context. As an illustration, the term "digital representation" might refer to a single digital representation or a set of digital representations. Additionally, "generating," a digital representation as used in this document, refers to the act of using computer calculation to construct a numerical representation of one or more objects. A file kept on a computer that contains numbers that reflect a three-dimensional projection of a dentition or dental arch, for instance, might make up the digital representation. In a further variant, the digital representation consists of a data collection with computer-usable parameters.

The present disclosure will be explained in terms of embodiments and specific drawings, but the invention is not restricted to these. The drawings given are simply schematic and not exhaustive. For illustration purposes, the size of some of the elements in the drawings may be exaggerated and not drawn to scale.

In some embodiments, the procedures and systems can be utilized to create a digital orthodontic treatment plan based on an interactive process, described herein with examples and modifications. These examples and variants of techniques and systems can be used to create a digital treatment plan for a patient's dentition. These techniques and tools are explained in detail with reference to the illustrative process for an interactive digital treatment plan shown in FIG. 3, which may be used, for example, in the production of dental appliances and/or the design of dental treatments.

Figure 2:
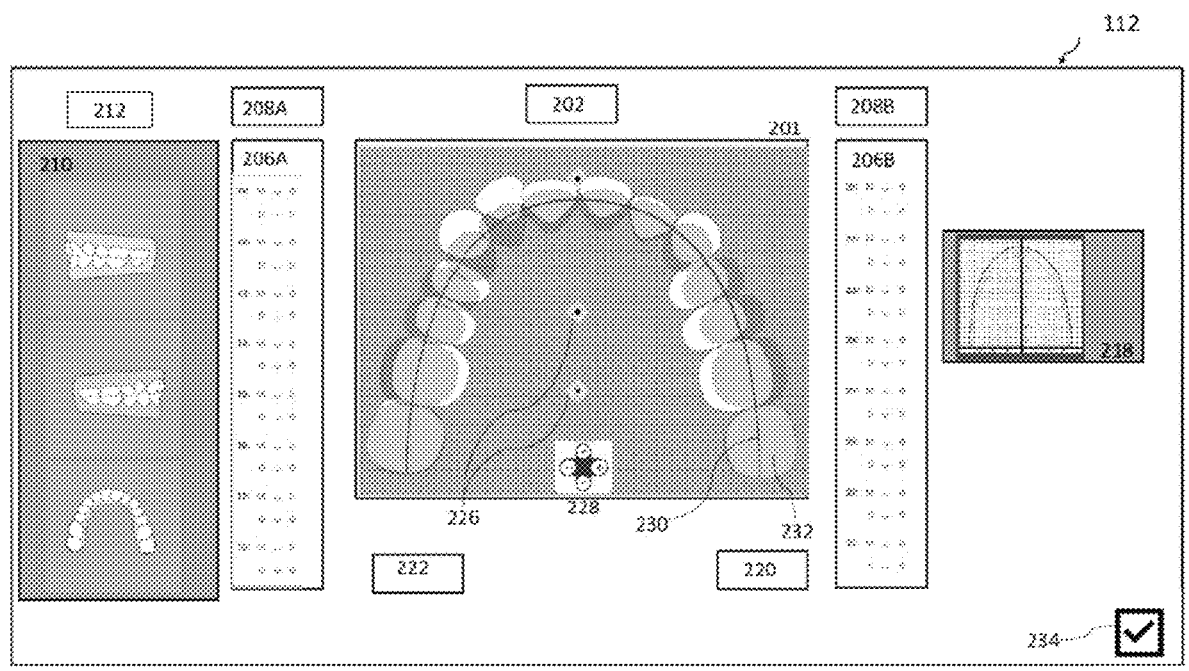
FIG. 2 shows a schematic presentation of an exemplary embodiment of a user-interface for use in an interactive process for generating a digital orthodontic treatment plan.
Figure 3:
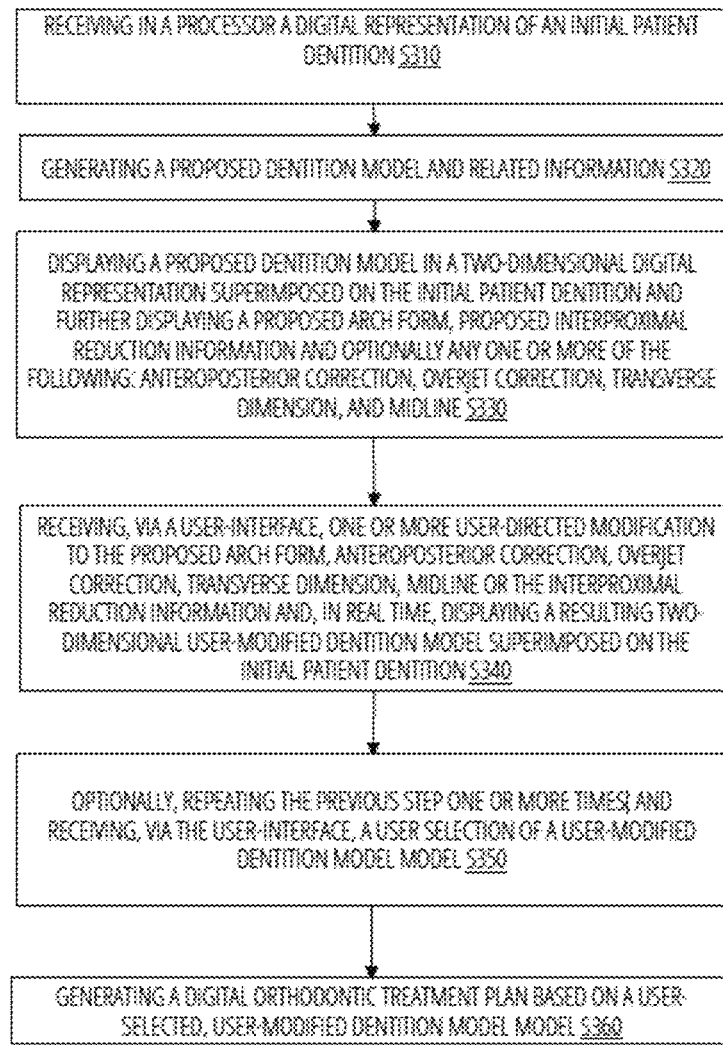
FIG. 3 shows a flow chart of an interactive process for generating a digital orthodontic treatment plan.

Several variations of the illustrative system or procedure for producing dental treatment plans, seen in the system of FIG. 1 or the flowchart of FIG. 3, are discussed in detail to exemplify these techniques and tools, which may be used, for example, in the production of dental appliances and/or the design of dental treatments. Variations of this procedure may include additional processes and apparatus that are not shown in addition to or instead of those that are shown in FIGS. 1, 2, 3, 4 and 5. The steps do not have to be carried out in the sequence shown. Additionally, the arrangement of the digital representation in FIG. 5 is only one example of a number of possibilities. Any person with ordinary skill in the field who has the benefit of this disclosure will be able to understand that different iterations of these techniques and equipment for creating digital models of a patient's tooth arrangements may also be used in other dental applications.

As used herein, the term "comprises", "includes" and its variants have no limiting meaning when those terms appear in the description and claims. These terms are to be understood to mean the inclusion of a particular step or element or group of steps or elements, but not the exclusion of any other step or element or group of steps or elements. All elements or combinations of elements listed in this specification in open language (e.g., "comprise" and derivatives thereof) are also considered to be listed in closed language (e.g., "consist of" and derivatives thereof) and in partially closed language (e.g., "consist essentially of" and derivatives thereof).

The use of phrases such as "one embodiment," "an embodiment," "certain embodiments," "one or more embodiments," "various embodiments", "one aspect," "an aspect," or "some embodiments" throughout this specification means that a particular feature, configuration, composition, or characteristic described in connection with the embodiment is included in at least one embodiment of the disclosure.

As used herein, the term "or" is generally used in its ordinary sense, including "and/or" unless the content clearly dictates otherwise. The term "and/or" means any or all of the listed elements or a combination of two or more of the listed elements.

Some terms used in this application have a special meaning, which is defined herein. All other terms are known to a person skilled in the art and have the meaning that a person skilled in the art would have given them at the time of the invention.

As used herein, a user may relate to a dental professional, orthodontist, or practitioner.

As used herein, "dentition" refers to the arrangement, number, and types of teeth in a patient's mouth. In the context of the present invention, dental treatment planning is designed to improve or modify a person's initial dentition. Throughout the disclosure, different states of dentition will be described, such as initial patient dentition, proposed state dentition, and user-modified dentition. Each of those states may have a suitable model being a digital representation of the dentition in that state.

As used herein, "initial patient dentition," "initial dentition," or "initial patient dentition" refers to an initial patient dentition or model thereof prior to initiating the present treatment. In some embodiments, the initial patient dentition is the initial patient dentition for this treatment round even if the patient has undergone previous orthodontic treatment.

As used herein, "interproximal reduction" refers to a dental procedure in which small amounts of tooth enamel are removed from the sides of teeth, typically the mesial or distal surface, to create more space for alignment. Interproximal reduction information is the amount of reduction required to resolve dental crowding. Interproximal reduction information can generally relate to the volume of tooth enamel removed or the distance shaved from the distal or mesial end. The calculation is based on the arch form and crown widths or, specifically, the mesiodistal width of the tooth's anatomical crown. The degree of dental crowding is the difference between the total mesiodistal crown widths of the teeth and the length of the initial arch form. In a normal tooth arrangement, the degree of dental crowding should be zero. A positive value of this difference indicates the presence of crowding, while a negative value indicates the presence of gaps. By slightly polishing and shaping of the adjacent faces of a plurality of teeth, the contact relationship between closely adjacent teeth in the dentition disappears, and gaps between teeth are formed.

The information may be broken down into mesial or distal, total tooth, half arch, total dentition, or upper plus lower dentition.

As used herein, a "proposed," "proposed state model" or "perturbed state model" is a processor-generated state of a dentition which may be displayed in two or three dimensions, in which a single tooth or set of teeth have undergone movement or a change in positioning. The proposed state dentition may be referred to as a perturbed state in that it is the predicted state resulting from modifications to a natural progression of dentition shifting. The proposed-state dentition is a processor projected model, generated based on a process or generated orthodontic treatment plan. The state of the shifted set of teeth, in the proposed-state dentition model, is necessarily different from an initial dentition and different from a natural progressed state.

As used herein, the term "superimposed" refers to arranging an initial patient dentition model of the initial dentition and a second digital dental model of the proposed-state dentition in a fixed spatial relationship, wherein a first data set corresponding to the first digital dental model and a second data set corresponding to the second digital dental model are maintained as different data sets after superimposing. In some embodiments, different data sets are maintained after superimposing without merging the first data set (i.e., of the initial dentition) and the second data set (i.e., of the proposed-state dentition). In some embodiments, a fixed spatial relationship is such that the first digital dental model and the second digital dental model are aligned when viewed from a viewpoint and are maintained as separate representations after the arrangement. The fixed spatial relationship may be based on anatomical and/or geometrical correspondence of the first digital dental model and the second digital dental model. Thus, the fixed spatial relationship may ensure that the two models are displayed from the same perspective.

"Anteroposterior correction" refers to the assessment and planning pf interventions aimed at correcting the alignment and positioning of teeth in the anterior-posterior dimension. This involves analyzing the relationship between the upper and lower jaws, assessing the way upper and lower dentition fit together, and determining the adjustments or treatment to achieve proper alignment and bite function. This correction addresses issues such as overbite, underbite, crossbite and other malocclusions for optimal aesthetics and dental health.

"Overjet correction" refers to the process of reducing or correcting the horizontal overlap between the upper and lower front teeth. Overjet in this context, is the measurement of how far the upper front teeth protrude horizontally beyond the lower front teeth.

The "transverse dimension" refers to the extent of expansion in the posterior teeth region of the dental arch. For example, one may specify the desired range of expansion, or provide control over the width of the dental arch to achieve optimal alignment and occlusion. Useful details can be found in Andrews, L. F., (1972). The six keys to normal occlusion. *American Journal of Orthodontics*, 6 (3). https://doi.org/10.1016/S0002-9416(72)90268-0.

"Midline" refers to an imaginary vertical line that divides the face and dental arches into left and right halves. Specifically, the dental midline is the line that divides the upper and lower dental arches into symmetrical halves.

"Incisor midline" refers to an imaginary vertical line that bisects the central incisors in the upper and lower dental arches and represents the alignment of the central incisors in relation to the facial midline.

As used herein, a "user-modified dentition model" is model resulting from user modification or alteration of a proposed or perturbed state dentition model. It is a processor generated digital representation of a dentition, resulting from user modification or alteration of a proposed-state dentition model. The digital representation of this dentition model is two dimensional.

As used herein, a "user-selected user-modified dentition model" or for short, a "user-selected dentition model" is the user selected model from the various user-modified dentition models which are displayed for the user.

According to one aspect, the systems and methods described herein relate to a computer-implemented method for interactive digital orthodontic treatment planning executed by a processor based on interactive modification input from a user. In various embodiments, the systems and methods described herein include one or more user-interface features allowing the user to modify the arc form or interproximal reduction information of a treatment plan.

In some embodiments of the methods or systems described herein, a data processing system is disclosed. The data processing system includes modules or computation units such as a processor that are configured to perform one or more steps of the method disclosed in one or more embodiments of this disclosure. The data processing system may include other modules such as memory.

Referring now to FIG. 1, a block diagram of a computerized device for implementing the methods of the present invention is presented. System 100 is described herein for interactive digital orthodontic treatment planning. System 100 may be configured as a personal computer, workstation, or mainframe. The system may include a display device 112. Display device 112 refers to a user-interface output device configured to communicate information to a user, typically by way of a visual presentation using a screen or tablet, although it may additionally involve an audio output. System 100 may further include a processor 108 and memory 109 coupled to the processor 108. Memory 109 may be a storage unit or cloud-based memory connected to a server and configured to direct processor 108 to make a list of actions. Memory 109, including cloud storage, is well-established in conventional protocols and computer architectures.

System 100 is configured to receive a digital model of initial dentition; generate a proposed digital model of dentition and related information; display the proposed digital model of dentition in a two-dimensional digital model superimposed on the digital model of initial dentition as well as related information, receive modifications directed by user via a user interaction interface, receive a user selection of a user-modified digital model of dentition via the user interaction interface, and generate a digital plan for orthodontic treatment based on a user-selected and modified digital model of dentition. Related information which may be displayed in proposed-state and user-modified include the following: interproximal reduction information, arch form, anteroposterior correction, overjet correction, transverse dimension, and midline.

User modifications may be repeatedly received, by the processor, which may be local, and according to the user's preference. In various embodiments, processor 108 may be directed to receive input, being a digital representation of an initial patient dentition 102. Processor 108 may then be directed to generate a proposed dentition model for digital planning on display device 112. Processor 108 may be directed to display a digital representation of the proposed dentition model, superimposed on the initial patient dentition model. Processor 108 may be directed to display the associated interproximal reduction information.

In various embodiments, display device 112 presents the arch form of both dentition models, i.e., proposed perturbed-state and initial patient-state dentition, which may be either superimposed or in a dedicated region of the user-interface. In various embodiments, a display of the proposed interproximal reduction information associated with the proposed dentition model is also present. The information may be displayed on a total dentition basis, on a per tooth basis, or alternatively on a per surface basis (i.e., distal, and mesial).

In various embodiments, the processor may be directed to, based on one or more user-directed controls in the user-interface 110, receive, by the processor 108, one or more user modifications to the arch form and/or the interproximal reduction information and subsequently generate and display a digital representation of a user-modified dentition model based on the input received.

In various embodiments, processor 108 may be directed to, based on one or more user-directed controls in the user-interface 110, receive, by the processor 108, one or more user modifications to any one or more of the following proposed-state dentitions: interproximal reduction information, arch form, anteroposterior correction, overjet correction, transverse dimension, and midline, and subsequently, generate and display a digital representation of a user-modified dentition model based on the input received.

In various embodiments, processor 108 may be directed to, based on one or more user-directed controls in the user-interface 110, receive, by the processor 108, one or more user modifications to the anteroposterior correction, overjet correction, transverse dimension, and midline and display the resulting associated interproximal reduction information.

User modifications may be repeatedly received, according to the user's preference. In various embodiments, processor 108 may be directed to display, in a region, a two-dimensional digital representation of a user-modified dentition model, associated arch form, and interproximal reduction information. In various embodiments, processor 108 may be directed to display, in a region, a two-dimensional digital representation of a user-modified dentition model, interproximal reduction information and one or more of the following: anteroposterior correction, overjet correction, transverse dimension, and midline.

In various embodiments, processor 108 may be adapted to, in real-time, toggle between one or more two-dimensional digital representations of the user-modified perturbed-state dentition model, with associated information such as the interproximal reduction information. The processor 108 may be directed, based on one or more user-directed controls in user-interface 110, to receive, a user selection of a user modified proposed dentition model. Subsequent to the user selection, processor 108 may provide an output, being an orthodontic treatment plan 106 based on the user-selected dentition model.

Figure 4:
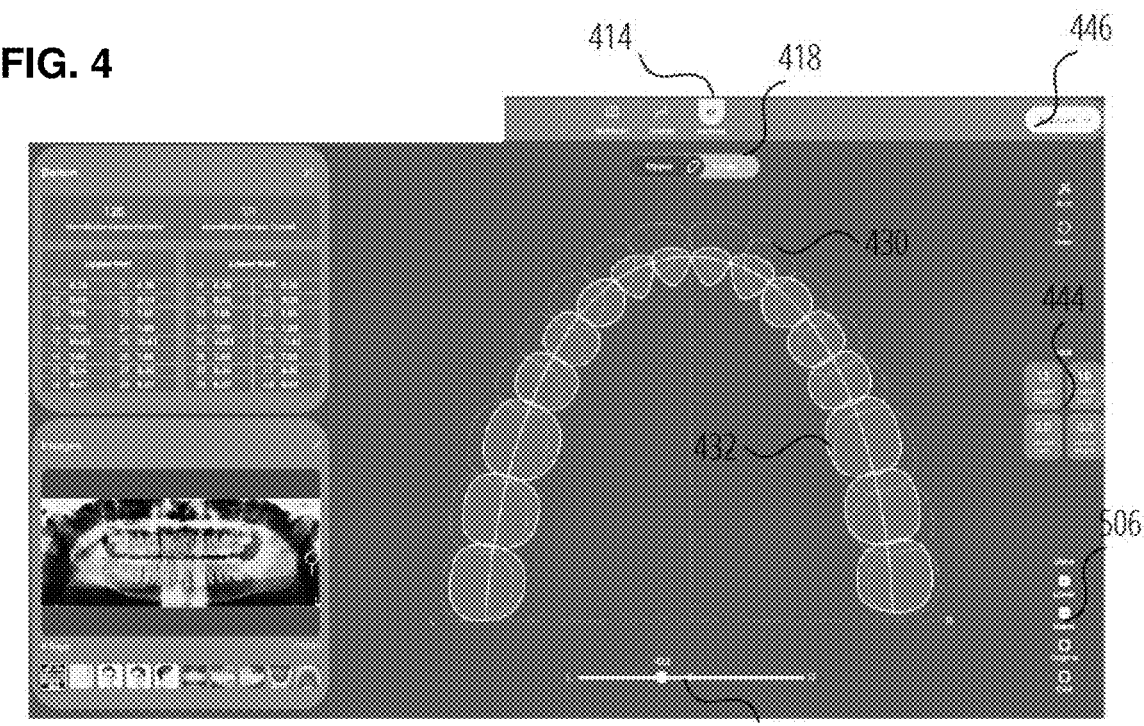
FIG. 4 shows a schematic presentation of an exemplary embodiment of a user-interface for use in an interactive process for generating a digital orthodontic treatment plan.
Figure 5:
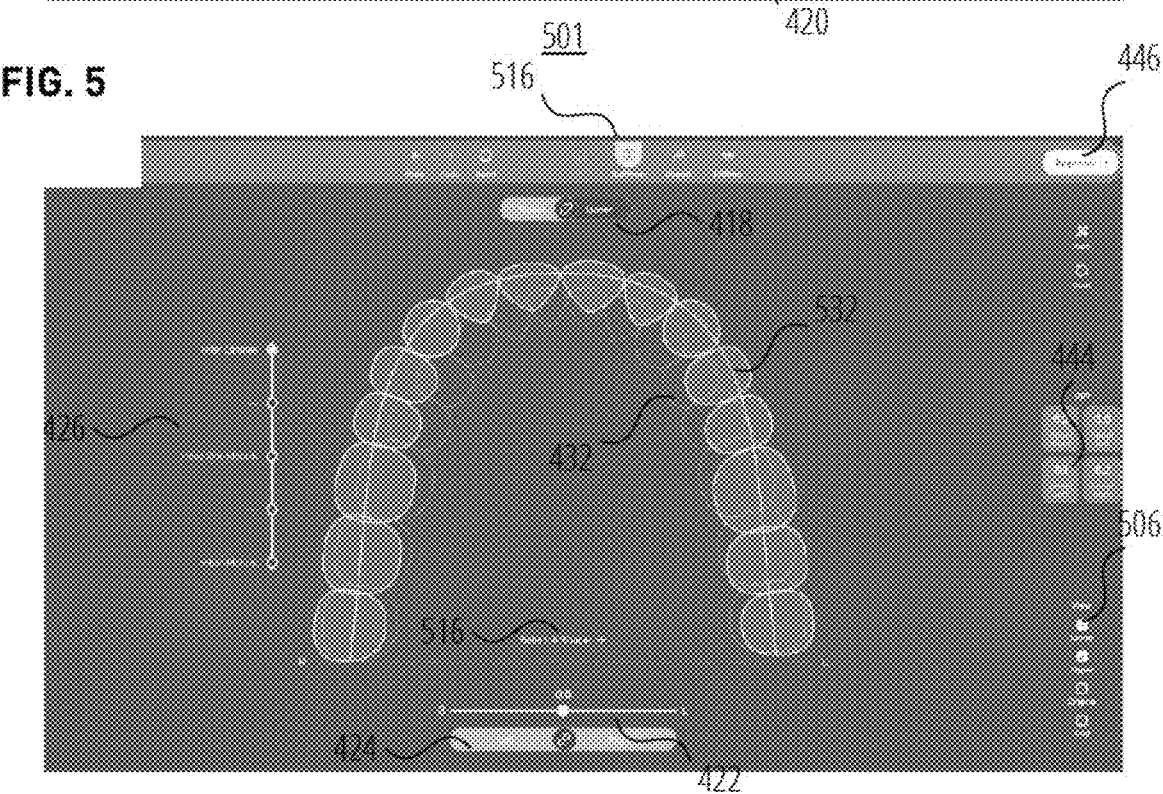
FIG. 5 shows a schematic presentation of an exemplary embodiment of a user-interface for use in an interactive process for generating a digital orthodontic treatment plan.

For illustrative purposes, FIGS. 2, 4 and 5 are examples of a graphical user-interface (GUI) display, generated by the processor and displayed on the display device 112. The figures schematically provide examples of the different regions, such as region 201, 401 and 501, each with graphical user-interface (GUI) features presented at a computing device to interface with the user, for example, in selecting and modifying features of the arch form interproximal reduction, or alternatively, finalizing a selection of a user-modified model.

In region 201, 301 and 401, a display is provided in two dimensions of a proposed-state dentition model 332 superimposed on an initial patient dentition model 330. For example, one may employ a drawing technology and Bezier curve with two control point per half arch. The proposed state dentition display are based on Bolton analysis (i.e., mesial distal and bucco-lingual sizes). Alternatively, it may present in two-dimension, after certain stages of the process, a user-modified dentition model 432 superimposed on an initial dentition model 430.

An arch form 230 may also be presented, although it may be removed. Multiple user-interface features may be provided to allow the user to alter the arch form in the perturbed proposed state model.

In some implementations, control points 226 are shown as spheres. However, the control point 226 can be any other type of graphical indicia. In some implementations, both control points 226 and 228 cooperate to adjust the arch form such that it is possible to expand or contract the distance between any number of opposing teeth in a dentition at various locations or adjust the curvature. In some implementations, user-interface 202 can be configured to accept input provided by the user and optionally enable toggling between the different types of resulting user-modified dentitions. Modification of the form may include a modification that is symmetric or a left or right adjustment of the arch. In some implementations, the arch form 230 may be modified independently of the dentition model 232. The user-interface 202 may be configured to receive one or more inputs described herein from the user to then cause the dentition model 232 to align to the arch form 230.

In various embodiments of the methods or systems described herein, the method may include receiving, via user-interface 202, input on one or more user-directed modifications to the proposed arch form and/or to the interproximal reduction. The user-directed modifications may be one or more of the following: expansion or contraction of the arch form 230 form, shifting a center of an arch form, interproximal reduction on a dentition, interproximal reduction on a per tooth basis, or interproximal reduction per mesial or distal surfaces of the tooth.

In various implementations of the methods or systems described herein, the method may include receiving, via a user-interface 202, input on one or more user-directed modifications to the interproximal reduction such as a user-directed modification in the interproximal reduction being one per tooth basis, an interproximal reduction per mesial surface of an individual tooth, or interproximal reduction pedestal surface of an individual tooth. Other modifications are also possible, such as adding or subtracting an amount from interproximal reduction on a per tooth basis. In another example, adding or subtracting an amount from the interproximal reduction from a mesial surface of an individual tooth. Alternatively, adding or subtracting an amount of interproximal reduction from a distal surface of an individual tooth.

In other implementations, user-interface 222 and user-interface 220 can be configured to accept inputs provided by the user for adjusting the two-dimensional view in region 201. For example, user-interface 222 can be configured to accept inputs provided by the user to toggle a view of an arch form, dentition, or both. In some implementations, user-interface 220 can be configured to accept inputs provided by the user for toggling a view between an initial state or user-modified state dentition.

In region 210, a user-interface 212 can be configured to accept inputs provided by the user to select any one of a variety of views of any dentition. The views in region 210 may be presented in one or multiple windows with a top view, bottom view, right view, left view, or a combination thereof.

Interproximal reduction may be altered in user-interface 202, user-interface 208 and/or user interface 206. User-interface 202 provides a user-interface to numerically adjust the total interproximal reduction. User-interface 208A and user-interface 208B, may enable numeric adjustment of the interproximal reduction of the total left or right side of the dentition model.

Alternatively, user-interface 208A and user-interface 208B may employ color or other indicators which may indicate that the total interproximal reduction information requires an adjustment of the individual tooth based interproximal reduction information. In this case, a user may be required to resolve the inconsistency.

In some implementations, user-interface 206A and user-interface 206B, the individual values of the mesial or distal surface of each tooth can be modified. Although the display-on-display device provides a number of options, it is to be recognized that different embodiments of the present invention may involve only one or more of the user-interfaces presented which may control modifications to the interproximal reduction information.

In some implementations additional regions may be dedicated to any one or more user-interfaces which support the interactive method. For example, in region 218, an initial and proposed-state or user-modified arch form may be displayed. Alternatively, or additionally, the upper and lower arch form of the perturbed state (i.e., proposed or user-modified) may be displayed. Interestingly, the two-dimensional representation provides an effective means of providing sufficient data to the user in the user-modification stage.

In some embodiments, a series of previous user-modified perturbed state dentition models may be viewed in order to enable sequential improvements.

In user-interface 234, an example of a user-interface feature is provided which may receive a selection by the user of a specific user-modified dentition model.

Referring now to FIG. 3, a flow chart of a computer-implemented method for interactive digital orthodontic treatment planning is presented. The computer-implemented method is configured to generate an output of a digital orthodontic treatment plan based on the user-selected perturbed-state dentition. wherein all steps of the process are performed locally.

In some embodiments, the process includes the following steps: at step S310, receiving, in a processor, a digital representation of an initial patient dentition, prior to initiating the dental treatment plan; at step S320, generating a proposed dentition model, proposed arch form, interproximal reduction information and related information; at step S330, displaying the proposed dentition model in a two-dimensional digital representation, superimposed on the initial patient dentition model, and further displaying a proposed arch form, proposed interproximal reduction information and optionally any one or more of the following: anteroposterior correction, overjet correction, transverse dimension, and midline; at step S340, receiving, via a user-interface, input on modifications of parameters and in real time, displaying the resulting user-modified dentition model, being superimposed on the initial patient dentition model; at step S350, receiving, via the user-interface, a user selection of a user-modified dentition model; and at step S350, processing and outputting from the processor, an orthodontic treatment plan based on the user-selected dentition model (i.e., three-dimensional representation of a treatment plan) based on the user-selected dentition model. The treatment plan will typically refer to incremental position towards the user-selected dentition model. In various embodiments, S340 may be repeated a number of times prior to selection. In various embodiments, the user-interface includes two-dimensional controls superimposed on the display. In some cases, the user-interface will communicate when a user-modification goes beyond any given threshold.

In various embodiments of the methods or systems described herein, at step S310, receiving in a processor a digital representation of an initial patient dentition may include receiving in a processor a three-dimensional digital representation of an initial patient dentition. In some embodiments, receiving in a processor may be provided by a variety of means. In some embodiments, the three-dimensional digital representation of an initial patient dentition may be obtained directly by optically scanning using a dental X-ray scanner to provide an intraoral digital scan of the patient's teeth or alternatively, indirectly by scanning a physical dentition model created from a negative impression of the patient's teeth. In some embodiments, the receiving of the digital representation is by importing, typically in response to a user selection, from a database.

In various embodiments of the methods or systems described herein, at step S320, generating a proposed or perturbed-state dentition model may refer to generating, typically based on an algorithm, a proposed dentition model and related information. This step is well established in the art of orthodontic treatment planning and is typically automatically generated and provided as a single, fixed final proposed dentition which is predicted to result from modifications to a patient's dentition from an initial position based on a series of aligners.

In various embodiments of the methods or systems described herein, at step S330, displaying proposed interproximal reduction information and, further displaying a two dimensional proposed perturbed-state dentition model having a proposed arch form, and being superimposed on the initial patient dentition model is provided. In some embodiments, each model i.e., initial patient dentition model and the proposed perturbed-state dentition model, include an arch form or include a region for display of the associated arch form. Displaying may be on a display device 112 associated with the processor. The displaying may be a two-dimensional digital representation of either a patient's upper or lower dentition or enable toggling a button to switch between the two. The displaying may include the proposed perturbed-state dentition model being superimposed on the initial patient dentition model to enable to user to compare and analyze.

In various embodiments of the methods or systems described herein, displaying further includes a view of the proposed perturbed state arch form or user-modified perturbed-state arch form and an opposing dentition arch form. In some embodiments, additionally and specifically displayed is any one or more of the following: anteroposterior correction, overjet correction, transverse dimension, and midline. In some embodiments, additionally and specifically displayed is two or more of the following: anteroposterior correction, overjet correction, transverse dimension, and midline.

In some embodiments, additionally and specifically displayed is three or more of the following: anteroposterior correction, overjet correction, transverse dimension, and midline.

In some embodiments, additionally and specifically displayed is four or more of the following: anteroposterior correction, overjet correction, transverse dimension, and midline.

In some embodiments, the display of any one of arch form, anteroposterior correction, overjet correction, transverse dimension, and midline may be by user-direction selection of the specific parameter.

In various embodiments of the method or systems described herein, displaying further includes two or three-dimensional, upper, and lower side view of the patient's dentition.

In various embodiments of the methods or systems described herein, displaying may be simultaneously or selected by the user for display. In various embodiments of the methods or systems described herein, generating, and displaying by the processor, may also include an arch form on the initial patient dentition model, proposed perturbed-state dentition model and/or user-modified perturbed-state dentition model. As used herein, an arch form is a curve of a dental arch. Generally, teeth are arranged in an arch shape on the gums, following the alveolar bone. The upper jaw's arch curve connecting all teeth is called the maxillary curve of the dental arch, while the lower jaw's arch curve is called the mandible curve of the dental arch. Dental arch convexity, represented by the position of the incisors, can be measured cephalometrically. If the convexity decreases, there may be a gap, and if it increases, a gap may form. The dental arch width is measured in three sections: the width between cuspids, bicuspids, and molars, respectively. The width between cuspids measures the anterior section's width, the width between bicuspids measures the middle section's width, and the width between molars measures the posterior section's width. To obtain these measurements, the distance between the cusps of cuspids on both sides, the central fossa of the first bicuspids, and the first permanent molars' central fossa should be measured. The length of the initial dental arch is defined as the overall arch length of the arch that starts from the mesial contact point of the first molar of the lower jaw, extends over the buccal cusp of the premolars, the cusps of the lower cuspid, edges of lower incisors, and ends at the mesial contact point of the first molar of the upper jaw on the opposite side.

In various embodiments, the generating and displaying by the processor, may also include the interproximal reduction information associated with the proposed-state dentition or more specifically with a specific arch form shape.

The interproximal reduction information is typically associated with a proposed-state dentition, i.e., proposed perturbed-state dentition or user-modified perturbed-state dentition. In the context of treatment planning, the processor is configured to identify two adjacent teeth which are candidates for prescribing interproximal reduction. The processor would propose a digital dental model having a desired arch form with an overlap in a target position, identify a reference line on each of the adjacent teeth tooth, revise the treatment plan wherein a position of each of the adjacent teeth is determined in which the reference line of the each of the teeth are aligned without overlap, and prescribing interproximal reduction based on the determined position of each of the teeth.

In some embodiments of the methods or systems described herein, the interproximal reduction information displayed is a sum of reduction information on a per tooth basis. In some embodiments, the interproximal reduction information displayed is a sum of reduction information on an upper or lower dentition. In some embodiments, the interproximal reduction information displayed is a sum of reduction information on a half arch basis. In some embodiments, the interproximal reduction information displayed is a sum of reduction information on a total dentition, i.e., upper as well as lower dentition.

At step S340, receiving, via a user-interface, input on modifications of parameters of the proposed arc form curve and/or the interproximal reduction information and in real-time, displaying the resulting modified perturbed-state dentition model, being superimposed on the initial patient dentition model. In various embodiments, the method may include receiving, via a user-interface, one or more user-directed modifications to the proposed arch form or the proposed interproximal reduction information and, in real time, displaying a resulting user-modified perturbed-state dentition model superimposed on the initial patient dentition model.

The interproximal reduction information is a crucial consideration for any dental practitioners. Each modification to the arch form, anteroposterior correction, overjet correction, transverse dimension, or midline may affect the interproximal reduction information. In order to optimize decision by the practitioner, a method which enables toggling between different modifications, for example, of the arch form shape, and viewing the associated interproximal reduction in each case, can contribute significantly to decision making. Interestingly, outcomes were enhanced by providing a processor having the ability to modify and display, in real time, the effect of any specific modification on the interproximal reduction information.

In various embodiments, the processor receives user input on modifications to the arch form and/or to the interproximal reduction information to generate a user-modified perturbed-state dentition model. Alternatively, the processor receives user input on modifications to any one or more of the following: arch form, anteroposterior correction, overjet correction, transverse dimension, and midline and/or to the interproximal reduction information to generate a user-modified perturbed-state dentition model.

In some embodiments, toggling by the user-interface of each resulting dentition model i.e., one or more user-modified perturbed-state dentition models may be possible to enable the user to view multiple user-modified perturbed-state dentition models during a process of selection. In some embodiments, the user-modified perturbed-state dentition model may be superimposed on the initial patient dentition model.

In various embodiments, step S340 maybe repeated any number of times until the user is satisfied and prepared for the selection stage.

At step S350, receiving, via the user-interface, a user selection of a user-modified perturbed-state dentition model. In some embodiments, a user selection of a user-modified perturbed-state dentition model is based on one or more user controls in a user-interface, which is receiving by the processor. The selection may be a user-selected perturbed-state dentition model from the one or more user-modified perturbed-state dentitions generated in step S340 or in a repeated S340.

A step S360, processing and outputting from the processor, an orthodontic treatment plan based on the user-selected perturbed-state. In another aspect, the methods described herein relate to a computer-implemented method for interactive digital orthodontic treatment planning executed by a processor and adapted for user directed modification, the method including: receiving in a processor a digital representation of an initial patient dentition; generating and displaying by the processor: a two-dimensional digital representation of a proposed perturbed-state model for digital planning of a patient's upper or lower dentition, superimposed on an initial patient dentition model, wherein both dentitions (i.e., initial patient dentition model and proposed perturbed-state dentition model) may further include an arch form and interproximal reduction information associated with the proposed perturbed-state dentition; based on one or more user-directed controls, receiving, by the processor, one or more user modifications to the arch form and the interproximal reduction information and toggling by the processor, in real time, each of the resulting two dimensional top or bottom views of user-modified perturbed-state superimposed on the initial patient dentition model; based on one or more user-selected controls, receiving by the processor, user selection of a perturbed-state dentition model; and processing and outputting from the processor, an orthodontic treatment plan based on the user selected perturbed-state dentition model.

Referring now to in FIGS. 4 and 5, tab 418 is a selection of either upper or lower dentition while tab 414 or 516 is used to select a focus for a user-modification such as a selection of a midline adjustment in 414, or of an arch form adjustment in 516. In FIG. 4, upon selection of midline adjustment, a user may view the interproximal reduction information 444 for each half arch (upper left, upper right, low left, lower right) while shifting the midline using user interface 420 for the selected lower dentition 506. One can also view the initial dentition model 430 compared with the resulting user-modified dentition model 432. If satisfied, one may select, using interface 446, the user-modified proposed user-modified dentition 432.

Alternatively, or additionally, as demonstrated in FIG. 4, adjustment of an arch form may be selected in user interface 516. Upon selection of the arch form adjustment, a user may select any one or a number of shapes in 516 and view the resulting user-modified-proposed dentition model 532 with associated interproximal reduction information 544 for each half arch (upper left, upper right, low left, lower right), depending on selection in 506. Shapes for an arch form may be selected from tapered, square, ovoid, V-shape, or others which will be recognized by a practitioner in the dental field. The user may toggle between alternating shapes of a target arch form, for example, as preferred by a patient, using user interface 516 for the upper dentition. The user can select to shift left or right using 424 as well as the degree of shift in user interface 422. The user can also select a portion of the dentition to selectively alter in 426. One can also view the initial or previously user-modified dentition model 432 compared with the resulting user-modified dentition model 532. If satisfied, one may select, using interface 446, In various embodiments of the methods or systems described herein, the receiving in a processor a three-dimensional digital representation of an initial patient dentition and further includes receiving in a processor current case information. In some embodiments, the current case information includes patient information. Patient information may include information about the teeth such as extractions, tooth landmarks. In another embodiment, patient information may include general preferences of a user or dental professional such as preferred areas to maintain, focus or improve, preferred parameters for treatment such as tooth movement restrictions, preferred treatment duration, arch form preferences and patient concerns. In some embodiments, the current case information includes patient information and general preferences of a user or dental professional. The methods and apparatuses described herein may be further used to create and utilize a database of customized treatment preferences for users, which can be continuously updated as the user performs additional cases.

In various embodiments of the methods or systems described herein, upon receiving the case information, the next stage is generating and displaying by the processor, a two-dimensional digital representation of a proposed perturbed state. Generating is typically automatic and performed based on a set of algorithms know to the skilled in the art of orthodontic treatment planning. The perturbed-state model is meant to describe and/or illustrate a proposed, post treatment position of teeth which is an altered state compared to the initial patient dentition as well as altered from a normal path position if the initial patient dentition. For example, the perturbed-state model may be the result of rotating or moving a tooth or set of teeth within the digital two-dimensional model of teeth to generate the perturbed-state of the teeth. Alternatively, or additionally, the perturbed-state model may be the result of applying interproximal reduction to a tooth or set of teeth to generate the perturbed-state of the teeth. In some embodiments, the perturbed-state model may be the result of translating, rotating, and applying interproximal reduction to a tooth or set of teeth to generate the perturbed-state of the teeth. The perturbed-state model may be an automatically generated proposed final stage a treatment plan selected by the processor from the array of treatment plans. It should be understood that each of the perturbed-state models comprise a predicted model of the patient's teeth at a final stage for treatment plans having a plurality of sequential stages.

In various embodiments of the methods or systems described herein, the method includes generating and displaying by the processor a two-dimensional digital representation of a proposed perturbed state where the two-dimensional digital representation is typically the patient's teeth upper dentition or lower dentition at any one time. The two-dimensional digital representation of the perturbed state is superimposed on an initial patient dentition model. Displaying a two-dimensional digital representation of an initial patient dentition is a selective rendering of at least a part of the three-dimensional digital representation of an initial position received. In some embodiments, the two-dimensional digital representation of the perturbed state is superimposed on an initial position in a first zone. In some embodiments, both the initial and perturbed-state dentition further include an arch form typically positioned on the dentition outer surface. In some embodiments, the interproximal reduction information associated with the proposed perturbed-state dentition is also displayed.

In various embodiments of the methods or systems described herein, displaying is in a user-interface on a screen.

In various embodiments, the input provided by the user for relative movement can be achieved by directly interacting with either the two-dimensional controller or the superimposed model. This can include moving them manually by means of translation, zooming, rotation, etc. For example, a user input through a two-dimensional controller may rotate in the same direction by the same amount, translate in same direction by same amount, or apply the same magnification factor to both models simultaneously.

Alternatively, or additionally, the user can input a value for at least one movement parameter, which can be used by a processor to move either the two-dimensional controller or the superimposed model without requiring direct user interaction. The movement parameter can be associated with one or more movements, such as translation, rotation, zooming, etc. In both forms, the user's input for relative movement corresponds to a transformation.

In various embodiments, additional zones are also displayed and may include other information.

In various embodiments of the methods or systems described herein, the generating and displaying by the processor further includes an additional zone with a view of the proposed perturbed-state maxillary curve arch form and opposing dentition maxillary curve arch form, presented in region 218. In some embodiments, displaying further includes an additional zone with a view of the proposed perturbed-state mandible curve arch form and opposing dentition mandible curve arch form.

In some embodiments of the methods or systems described herein, the generating and displaying by the processor further includes an additional zone for displaying a three-dimensional proposed or user-modified state of an upper and lower side view. The side view may be of a patient dentition, upper and lower side view of a patient face, or upper and lower jaw radiographic view.

It should be appreciated that there is a correlation between the arch form and the interproximal reduction information. Although each of these parameters may be defined in advance of the treatment planning, these is value in having a dental practitioner, provide the desired balance between the two. For instance, a dental practitioner may wish to use his or her own judgment in altering the optimum balance or best compromised perturbed dentition between occlusion and alignment. In other cases, a patient may also be interested in providing input on preference. The ability to process and display this information in a user-friendly manner such that all relevant information is provided may enable a dental practitioner or patient to take part in the decision of the ideal cost-benefit balance to the patient.

In some embodiments of the methods or systems described herein, the method may include receiving in a processor the current case information, processing and displaying the relevant information and based on one or more user-directed controls, receiving, by the processor one or more user modifications to the arch form and the interproximal reduction information while enabling toggling by the processor, in real time (i.e., adjusting simultaneously or within 8 minutes for example), between each of the resulting two-dimensional top or bottom views of user-modified perturbed-state superimposed on the initial dentition. Toggling by the processor in real time may be within 10, 8, 6, 5, 4, 3, or 2 minutes.

In some embodiments of the methods or systems described herein, user-directed controls include an interface to adjust the interproximal reduction information on a per tooth basis. In some embodiments, one or more tools are provided which allow the user to modify the arch form or interproximal reduction information of a treatment plan. In some embodiments, user-directed controls include an interface to adjust the interproximal reduction information on a total dentition basis. In both cases, an adjustment in the interproximal reduction information results in an updated arch form. In some embodiments, user-directed controls include an interface to adjust the arch form. The user-directed controls may include buttons, sliders, tabs, etc. which may be on the display device. Alternatively, the controls may be off of the display device such as on a keyboard, mouse, trackball, glove, etc.

With each adjustment, the one or more user modifications are received by the processor while enabling toggling by the processor, in real time. The toggling by the processor would include switching, in real time, between images of the patient's teeth having alternative interproximal reduction information and arch form, in the proposed dentition model for different treatment plans. In some embodiments, switching between images of the patient's teeth in perturbed-state for different treatment plans based on one or more user-directed controls on the screen comprises switching a treatment plan having a specific interproximal reduction information or arch form with a treatment plan having different interproximal reduction information or arch form properties based on one or more user-directed controls on the screen. Toggling by the process in real time allows for a simultaneous adjustment in the display between each of the resulting two-dimensional top or bottom views of user-modified dentition model superimposed on the initial patient dentition model. The alternative variations of proposed dentition model models that are presented to the user (e.g., dental professional, or in some cases, the patient) in real time. For example, if a specific tooth is modified to a specific interproximal reduction information, a view of the displayed two-dimensional model will now include a modified or user modified perturbed dental model superimposed on the initial dental model. In some embodiments, additional zones which simultaneously also display the user selected modifications. The ability to toggle while displaying the different views, contribute to selecting a personalized treatment for the patient.

Toggling by the process in real time allows for a simultaneous adjustment in the display which can include user-modified dentition model superimposed on the initial patient dentition model in a number of different formats. For example, in one embodiment, a variety of user-modified dentition models may be presented in a side-by-side static manner and the user may visualize the models that are presented side-by-side.

In some embodiments, the method further includes, based on one or more user-selected controls, receiving by the processor, user-selected dentition model. In some embodiments, the user selection of a user modified perturbed dentition model is from any one of the automatically generated or user-modified projected patient dentition.

In various embodiments, a user may use digital buttons which indicate that a specific user modified proposed dentition model has been selected. User-interfaces 234 and 346 provide an example of a feature that may receive a user-modified dentition model selection by the user.

In various embodiments, the method may further include processing and outputting from the processor, an orthodontic treatment plan based on the user-selected dentition model. In alternative embodiments, the method may further include transmitting a selected perturbed model of the patient's teeth to a remote site. For example, the method may further include transmitting a selected perturbed model of the patient's teeth to a remote site and further comprise manufacturing or generating, at the remote site, an array of treatment plans specific to the patient's teeth.

In various embodiments, the orthodontic treatment plan may include different stages, wherein each stage corresponds to a different aligner to be worn for a predetermined period of time.

In various embodiments, the method includes processing and outputting from the processor, an orthodontic treatment plan based on the user-selected dentition model dentition model.

Typically, once a proposed dentition model is selected, it may be used to generate a series of three-dimensional models of dental appliances such as aligners based on the treatment plan according to the user modified perturbed dentition model. Generated in this context is meant to include processing and outputting from the processor an orthodontic treatment plan based on the user selected proposed dentition model which is a projected state dentition. Thus, in some embodiments, the orthodontic treatment plan, based on the user-selected dentition model dentition model, comprises a sequence of orderly steps where each stage comprises a different arrangement of a patient's teeth from the starting position to the target projected position directed by a sequence of aligners worn in successive stages making up the treatment plan. The three-dimensional models of the dental appliances can subsequently be used in providing instructions to form one or more aligners. A sequence of aligners refers to multiple aligners configured to direct a movement of a patient dentition through successive stages from the initial patient dentition to a user-selected dentition model.

In some embodiments of the methods or systems described herein, a computer program embodied in a non-transitory computer readable medium is disclosed. The computer program product includes computer readable program code being executable by a hardware data processor to cause the hardware data processor to perform a method when said computer readable program code is executed by the hardware data processor. The method may include one or more functions that allow one or more system components to perform one or more steps of the method disclosed in one or more embodiments of this disclosure.

All headings are for the convenience of the reader and should not be used to limit the meaning of the text that follows the heading, unless so specified.

In some embodiments of the methods or systems described herein, a data processing system is disclosed. The data processing system includes modules or computation units such as a hardware processor that are configured to perform one or more steps of the method disclosed in one or more embodiments of this disclosure. The data processing system may include other modules such as memory.

In some embodiments of the methods or systems described herein, a computer program product embodied in a non-transitory computer readable medium is disclosed. The computer program product includes computer-readable program code being executable by a hardware data processor to cause the hardware data processor to perform a method when said computer-readable program code is executed by the hardware data processor. The method may include one or more functions that allow one or more system components to perform one or more steps of the method disclosed in one or more embodiments of this disclosure. Those of skill in the art will appreciate that embodiments not expressly illustrated herein may be practiced within the scope of the claims, including that features described herein for different embodiments may be combined with each other and/or with currently known or future-developed technologies while remaining within the scope of the claims. This specifically includes that the structure, location, and mechanisms of the disclosed elements and related structures in the different embodiments illustrated and described with reference to the drawing figures may be combined and elements interchanged within the level of skill in the art as informed by this application, and within the scope of the present claims. Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

The invention claimed is:

1. A computer-implemented method for interactive digital orthodontic treatment planning executed by a processor, said method comprising:
   i. receiving in a processor, a digital representation of an initial patient dentition;
   ii. generating a proposed dentition model, the proposed dentition model being associated with information relating to a proposed interproximal reduction;
   iii. generating a simplified two-dimensional digital representation of the initial patient dentition and of the proposed dentition model, each said simplified two-dimensional digital representation including only an outline of each tooth and a length of the tooth in the mesial-distal direction;
   iv. displaying within a first region of a graphic user interface the simplified two-dimensional digital representation of the proposed dentition model superimposed on the simplified two-dimensional digital representation of the initial patient dentition;
   v. simultaneously with iv, displaying within the graphic user interface one or more numerical values corresponding to the proposed interproximal reduction, and one or more user-engageable interface elements configured for modifying one or more characteristics of the proposed dentition model in real time, the characteristics being selected from a list consisting of: an arch form, anteroposterior correction, overjet correction, transverse dimension, and midline;
   vi. receiving, via user engagement with one of the user-engageable interface elements of the graphic user-interface, user-directed modification to one or more of the arch form, anteroposterior correction, overjet correction, transverse dimension, midline, or the interproximal reduction of the proposed dentition model, and displaying, in real time and within the first region of the graphic user interface, a resulting simplified two-dimensional digital representation of a user-modified dentition model, superimposed on the simplified two-dimensional digital representation of the initial patient dentition;
   vii. receiving, via the graphic user-interface, a user selection of a specific user-modified dentition model selected from one or more user-modified dentition models generated by step vi; and
   viii. generating a digital orthodontic treatment plan based on the specific user-modified dentition model.

2. The computer-implemented method of claim 1, wherein the displaying of the one or more numerical values corresponding to the proposed interproximal reduction comprises displaying a numerical value representing a total sum of the proposed interproximal reduction of an upper dentition or of a lower dentition.

3. The computer-implemented method of claim 1, wherein the displaying of the one or more numerical corresponding to the proposed interproximal reduction comprises displaying a numerical value representing the total proposed interproximal reduction of each tooth, on a per tooth basis.

4. The computer-implemented method of claim 1, wherein the displaying of the one or more numerical values corresponding to the proposed interproximal reduction comprises displaying a numerical value representing a total sum of the proposed interproximal reduction of half a dentition arch.

5. The computer-implemented method of claim 1, further comprising displaying, within a second region of the graphic user interface, a digital representation of a first arch form of the proposed dentition model or of the user-modified dentition model, together with a corresponding opposing arch form of the proposed dentition model.

6. The computer-implemented method of claim 1, wherein receiving the one or more user-directed modifications comprises receiving a user-directed modification to the numerical value corresponding to the proposed interproximal reduction of the mesial surface of an individual tooth, of the distal surface of the individual tooth, or of the entirety of the individual tooth.

7. The computer-implemented method of claim 1, wherein receiving the one or more user-directed modifications comprises receiving a user-directed modification which adds or subtracts a numerical amount from the numerical value corresponding to the proposed interproximal reduction of an individual tooth, of the mesial surface of the individual tooth, or of the distal surface of the individual tooth.

8. The computer-implemented method of claim 1, wherein receiving the one or more user-directed modifications comprises receiving a user-direct modification to the arch form of the proposed dentition model, the user-directed modification including: (i) expansion or contraction of the arch form at one or more locations; and/or (ii) shifting a center of the arch form.

9. The computer-implemented method of claim 1, wherein receiving the one or more user-directed modifications comprises receiving, a user-directed modification to the anteroposterior correction of the proposed dentition model, the user modification specifying numerical values for factors teeth relationships.

10. The computer-implemented method of claim 1, wherein receiving the one or more user-directed modifications comprises receiving a user-directed modification to the transverse dimension of the proposed dentition mode, the user-directed modification specifying a desired range of expansion of the transverse dimension or controlling a width of the arch form to achieve improved alignment and occlusion.

11. The computer-implemented method of claim 1, wherein receiving the one or more user-directed modifications comprises receiving a user-directed modification to the overjet of the proposed dentition model, the user-directed modification being a modification to a horizontal overlap between an upper dentition and a lower dentition.

12. The computer-implemented method of claim 1, wherein receiving the one or more user-directed modifications comprises receiving a user-directed modification to the midline of the proposed dentition model, the user-directed modification being a modification to a horizontal overlap between an upper dentition and a lower dentition.

13. The computer-implemented method of claim 1, further comprising displaying, in an additional region of the graphic user interface, a two- or three-dimensional view of the initial patient dentition, the proposed dentition mode, or the user-modified dentition model, the two- or three-dimensional view including an upper and a lower side view of a dentition, an upper and a lower side view of a face, or an upper and a lower radiographic view of a jaw.

14. The computer-implemented method of claim 1, further comprising displaying, in an additional region of the graphic user interface, an initial occlusion relationship having a two dimensional initial and proposed-state dentition model and a user-modified occlusion relationship having a two dimensional initial and user-modified dentition model.

15. The computer implemented method of claim 1, further comprising toggling, by the graphic user-interface, between view of multiple user-modified dentition models generated by step vi.

16. The computer-implemented method of claim 1, wherein generating the digital orthodontic treatment plan comprises providing digital parameters to construct a sequence of aligners to be worn in successive stages, each aligner directing a movement of a patient dentition to a successive stage, the initial stage being the initial patient dentition and the final stage being the specific user-selected dentition model.

17. A system for interactive digital orthodontic treatment planning comprising:
(a) a processor;
(b) a memory coupled to the processor, configured to direct the processor to:
(i) receive a digital representation of an initial patient dentition;
(ii) generate a proposed dentition model, associated with information relating to a proposed interproximal reduction;
(iii) generate a simplified two-dimensional digital representation of the initial patient dentition and of the proposed dentition model, the simplified two-dimensional digital representation including only an outline of each tooth and a length of the tooth in the mesial-distal direction;
(iv) display within a first region of a graphic user interface, the simplified two-dimensional digital representation of proposed dentition model superimposed on the two-dimensional digital representation of the initial patient dentition;
(v) simultaneously with iv, display within the graphic user interface one or more numerical values corresponding to the proposed interproximal reduction and one or more user-engageable interface elements configured for modifying one or more characteristics of the proposed dentition model in real time, the characteristics being one or more of an arch form, anteroposterior correction, overjet correction, transverse dimension, and midline;
(vi) receive, via user engagement with one of the user-engageable interface elements of the graphic user-interface, user-directed modifications to one or more of the arch form, anteroposterior correction, overjet correction, transverse dimension, midline, or interproximal reduction of the proposed dentition model, and display, in real time and within the first region of the graphic user interface, a resulting simplified two-dimensional digital representation of a user-modified dentition model superimposed on the simplified two-dimensional digital representation of the initial patient dentition;
(vii) receive, via the graphic user-interface, a user selection of a specific user-modified dentition model selected from one or more user modified dentition models generated by (v); and (viii) generate a digital orthodontic treatment plan based on the specific user-selected dentition model.

18. The system of claim 17, wherein the processor is configured to display, as the one or more user-engageable interface elements one or more sliders.

19. The method of claim 1, wherein displaying of the one or more user-engageable interface elements comprises displaying, as the one or more user-engageable interface elements one or more sliders.

20. The method of claim 1, wherein the displaying, in real time, of the resulting simplified two-dimensional digital representation of the user-modified dentition model further includes displaying, in real-time, and updated value for the one or more numerical values corresponding to proposed interproximal reduction in the user-modified dentition model.

* * * * *